(12) United States Patent
Dogariu et al.

(10) Patent No.: US 6,587,206 B1
(45) Date of Patent: *Jul. 1, 2003

(54) METHOD FOR CHARACTERIZING PARTICLES IN A LIQUID MEDIUM USING INTERFEROMETRY

(75) Inventors: Aristide Dogariu, Winter Springs, FL (US); Gabriel Popescu, Orlando, FL (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,941

(22) Filed: Oct. 18, 2000

(51) Int. Cl.⁷ ................................................ G01B 9/02

(52) U.S. Cl. ......................................................... 356/479

(58) Field of Search ................................ 356/479, 497, 356/28.5, 480, 483, 460; 250/227.19, 227.27

(56) References Cited

U.S. PATENT DOCUMENTS 5,321,501 A * 6/1994 Swanson et al. ............ 356/479
5,710,630 A * 1/1998 Essenpreis et al. ......... 356/479
5,991,697 A * 11/1999 Nelson et al. .............. 356/28.5

OTHER PUBLICATIONS

Kokhanovsky, A. A., *Optics of Light Scattering Media Problems and Solutions*, John Wiley & Sons (1999), Table of Contents Only.

\* cited by examiner

Primary Examiner—Samuel A. Turner

(57) ABSTRACT

In a method for characterizing particles in a colloidal suspension, during a period in which the particles undergo sedimentation, changes are measured in the intensity among interference patterns generated by combining first and second partially coherent radiation portions. Each radiation portion is generated from the same source. The first portion includes a component transmitted through a fraction of the suspension, and the second portion is transmitted through a reference path.

9 Claims, 9 Drawing Sheets

EXPERIMENTAL SIZE DISTRIBUTION

D=(9.8, 10.6) m

METHOD FOR CHARACTERIZING PARTICLES IN A LIQUID MEDIUM USING INTERFEROMETRY

RELATED APPLICATIONS

This application is related to Ser. Nos. 09/690,904, 09/691,300, and 09/691,299, all filed on even date herewith.

FIELD OF THE INVENTION

The present invention relates to liquid-based systems containing particles and, more specifically, to systems and methods for characterization of particle components in mixtures.

BACKGROUND

Many processes and products include liquid media containing undissolved particles. The quantity and character of such particles in the media may be by design, may be an uncontrollable attribute, or may be a by-product resulting from the use of the media in a process such as cooling, lubricating, polishing or cleaning. The efficacy of a process or product incorporating such particles may be optimum when the concentration or character of such particles meets predetermined, albeit sometimes ideal, criteria.

The types of media which contain undissolved particles span a wide range of both industrial and consumer applications. Examples include blood, consumable liquids, industrial wastewater, lubricants and slurries, to name just a few. A specific example, for which exemplary embodiments of the invention are described below, is an abrasive slurry of the kind used for polishing a surface. It is desirable to characterize particle size and concentration in such media in order to provide more predictable abrasive properties. However, in some applications, the distribution of particle size and concentration is quite variable. Changes in these parameters are often very difficult or cumbersome to monitor, particularly during manufacturing processes. In some instances particle size distribution is so unstable as to cause unacceptable inconsistency in the process results. The instability is at times an inherent feature of the mixture. Controlling, or at least monitoring, the dynamics will also render processes more predictable and repeatable, thus adding further economic efficiency to the manufacture of products.

In abrasive media, it is not uncommon for the distribution of particle sizes to deviate from a preferred value. Under these circumstances, it is desirable to perform one or more inspections to assure such deviation is within acceptable tolerances. Initial inspections may use conventional analytical tools such as microscopy. However, the constraints of in-use monitoring may preclude application of the same analytical tools and thus such inspections may be limited to a form of visual observation. Observation of accumulated residue material is an indirect indicator that the composition of a mixture has changed.

Mixture instability is especially problematic in volume manufacturing operations, i.e., those requiring a high level of repeatability from one work piece to another. For example, when a timed polishing operation is expected to provide a predictable result, a change in the frictional characteristic of the polishing medium may so alter the polishing rate as to result in excess removal of material from the work piece or, perhaps, a nonuniformity across the workpiece. In many manufacturing applications such variations in a media characteristic occur at a pace which requires in-line monitoring. However, as already noted, conventional monitoring techniques are not well-suited for in-line applications.

Moreover, as the specifications for process steps become more demanding, conventional techniques may not have the ability to adequately resolve unacceptable variations. On the other hand, if attributes of liquid media, such as particle size distribution, rate of sedimentation and rate of agglomeration, were known with sufficient accuracy, then a wide variety of processes which utilize particles suspended in liquid media could be deployed with increased precision. There exists a need to improve the speed at which quantitative characterizations can be performed in order to provide relatively accurate and time-responsive results.

Further, it is often desirable to minimize, or at least monitor the size and quantity of, particles which enter lubricating media in order to sustain desirable properties. Thus, when the concentration or size of particulate matter rises above certain levels, the lubricant can be replaced or reconditioned. More generally, it is desirable to monitor entry of nonsoluble particles in liquid media. Suitable in-line techniques for continuously monitoring these characteristics would assure timely replacement of materials, facilitate maintenance activities and extend the life or efficiency of equipment.

SUMMARY OF THE INVENTION

To address the above-discussed needs the present invention provides a method for monitoring a characteristic of a mixture comprising a plurality of particles suspended in a liquid medium. Optical systems are provided for monitoring a colloidal suspension. An interferometric system and a method of characterizing particles in a colloidal suspension are also provided.

According to one embodiment of the invention, a method is disclosed for monitoring a characteristic of a mixture comprising a plurality of particles suspended in a liquid medium. First and second portions of radiation are generated from a source having a coherence less than one. Interference signals are generated by combining the portions after the first portion traverses a reference path and the second portion traverses a path extending into the mixture.

According to another embodiment there is an optical system for monitoring a colloidal suspension. The system includes a chamber positioned to receive a sample of the suspension while the suspension is circulating in a mechanical system. An interferometer is positioned to generate interference patterns developed by a combination of a reference radiation signal with a sample radiation signal indicative of a characteristic in the suspension.

An interferometric system includes first, second and third optical fibers with first and second couplers. The first coupler is configured to receive radiation through the first fiber, provide a first radiation portion through the second fiber and provide a second radiation portion through the third fiber to the second coupler. The system also includes fourth and fifth optical fibers each configured to receive radiation from the second coupler and transmit radiation for receipt by the other.

In a method for characterizing particles in a colloidal suspension, during a period in which the particles undergo sedimentation, changes are measured in the intensity among interference patterns generated by combining first and second partially coherent radiation portions. Each radiation portion is generated from the same source. The first portion includes a component transmitted through a fraction of the suspension, and the second portion is transmitted through a reference path.

DESCRIPTION OF THE DRAWINGS

The invention is best understood from the following detailed description when read in conjunction with the accompanying figures, wherein.

Like reference numerals correspond to like components or features throughout the figures. The figures are not drawn to scale.

DETAILED DESCRIPTION

Figure 1:
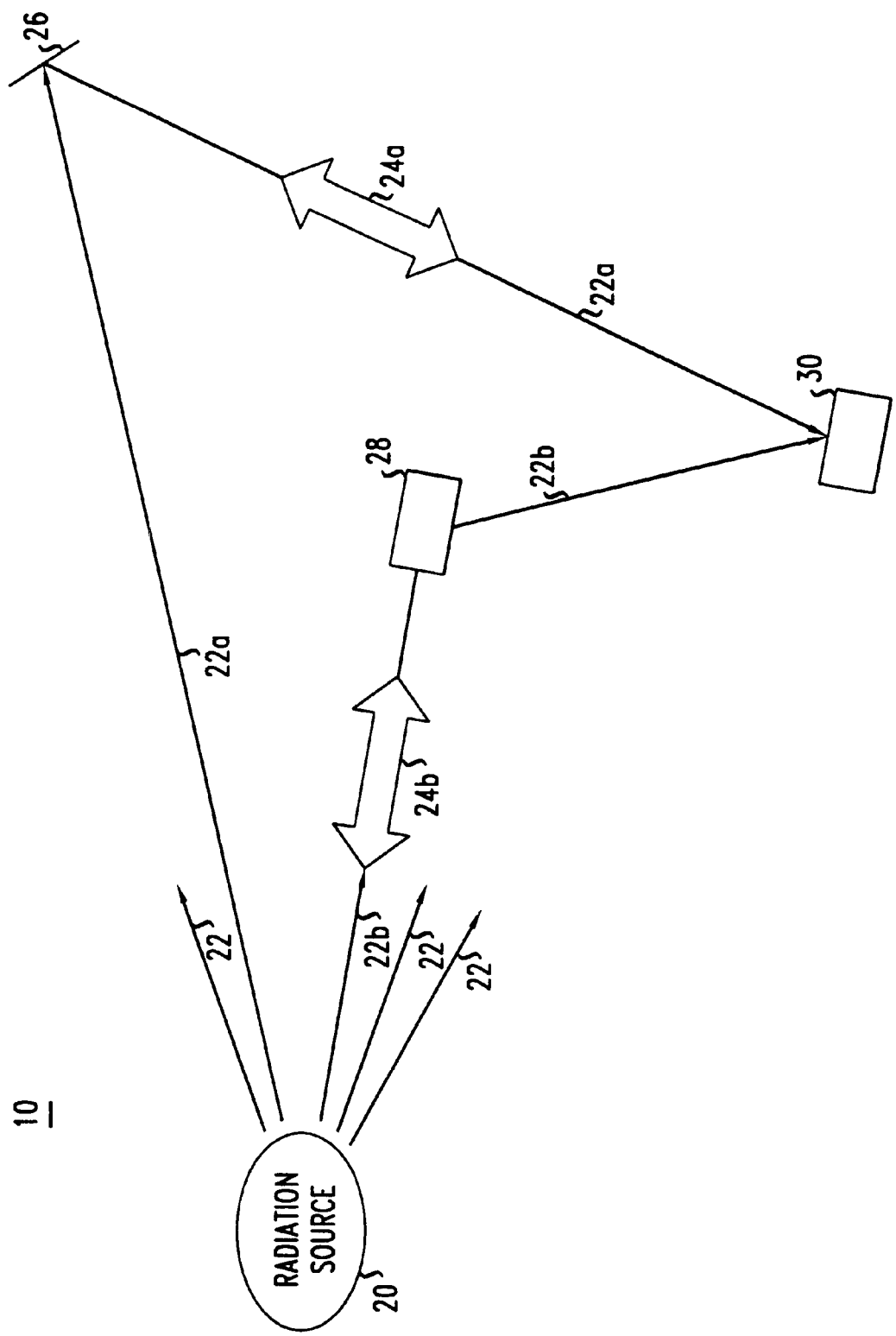
FIG. 1 schematically illustrates features of an optical system 10 suitable for determining characteristics of a mixture.

With reference to FIG. 1 an exemplary system 10, suitable for monitoring characteristics of a mixture, is illustrated according to the invention. A source 20 generates radiation 22 (generally indicated by arrows) having an optical coherence less than one and a center frequency $f_o$. A first portion 22a of the generated radiation traverses a reference path 24a, notationally indicated with a bi-directional arrow. The path 24a includes a reference position which may modify the path length. A second portion 22b of the generated radiation traverses a path 24b, also notationally indicated with a bidirectional arrow. The path 24b includes a liquid medium 28 not in the path 24a. The medium 28 contains suspended particles. After the radiation portion 22a reaches the reference position 26, and after the radiation portion 22b reaches the medium 28, the paths 24a and 24b become common such that the portions 22a and 24a are coincident upon reaching a detector 30.

The paths 24a and 24b are schematically illustrated in a manner which emphasizes that they may have little or no overlap after they depart from the source 20 and before they reach the detector. Bi-directional arrows reference radiation portions 22a and 24a to indicate that each may undergo reflection causing it to travel along a path segment more than once. For example, radiation portion 22b may be transmitted through or reflected from the medium 28. That is, the path 24b may pass through the medium or follow a reflective course from the medium. If reflected from the medium, the radiation may follow a same portion of the path, once in a first direction and then in a second direction, before reaching the detector 30.

Although not expressly shown, it should be recognized that the detector 30 could be positioned between the source 20 and the medium 28. This, for example, may occur when a portion of the traversed path is within a fiberoptic segment. Generally, the radiation portions 22a and 22b may be divided or combined in a variety of ways common to interferomteric techniques. Thus, the schematic notation for each of the paths 24a and 24b should be interpreted to contemplate any of numerous combinations of components and repeated sub-paths useful for transmitting, splitting, collimating, diverging and combining radiation in order to generate an interference pattern at the detector 30.

Figure 2:
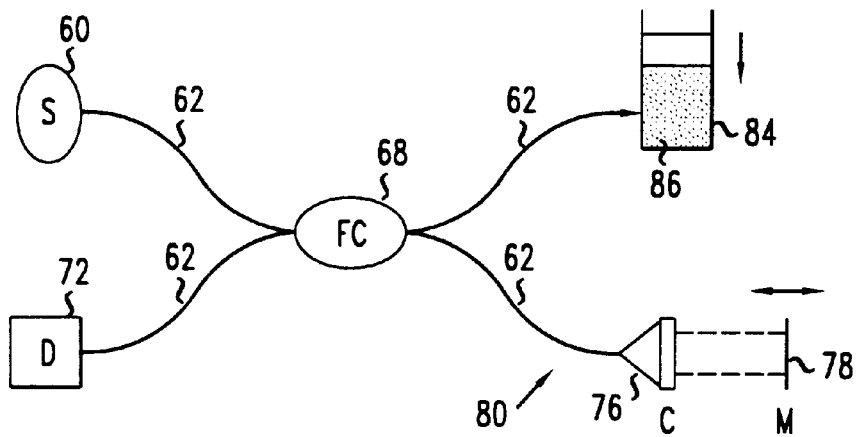
FIG. 2 presents in greater detail an exemplary system for determining a mixture characteristic according to the FIG. 1 illustration.
Figure 2:
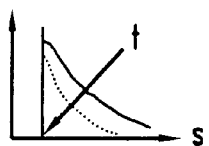

As discussed herein with specific examples the system 10 provides optical information from which physical characteristics of the medium 28 may be determined. Characteristics which may be determined from interferometric data generated by the system 10 include colloidal stability, sedimentation rate, and particle size distribution. In a more detailed example based on the system 10, the system 50 of FIG. 2 comprises a broadband source 60 such as a superluminescent diode that emits light with a central wavelength of 1.33 micrometers and a FWHM (Full Width at Half Maximum) bandwidth of 60 nanometers. Light emitted from the source 60 is coupled directly into one of several single mode optical fibers 62 to a first input/output side of a two-by-two fiber coupler 68. The light follows multiple paths along three other segments of fiber 62. From the same side of the coupler 68 as the source 60 is connected, a second of the fibers 62 is connected to a detector 72. Third and fourth of the fibers 62 are coupled to a second input/output side of the coupler 68. One such segment of fiber 62 forms, in conjunction with a collimator 76 and a mirror 78 spaced apart from the collimator 76, a reference arm 80 for providing a reference signal $S_R$. Thus $S_R$ traverses a reference path along three of the fibers 62 from the source 60 to the detector 72, corresponding to path 24a of FIG. 1.

The fourth segment of fiber 62 extends toward a sample housing 84 containing a mixture 86 of undissolved particles in a liquid medium. The sample housing 84 may be an open vessel or chamber or a conventional closed chamber, with one or more suitably transmissive optical flats. The illustrated housing is open.

A portion of light emanating into the housing 84 is reflected, e.g., backscattered, from particles suspended in the mixture such that the portion re-enters the associated fourth optical fiber 62. Depending on the concentration of suspended particles in the mixture, the reflected portion may undergo substantial back scattering, this resulting in propagation of light along multiple paths of differing length in the mixture.

The housing 84 and associated fourth fiber 62 form a sample arm to provide a sample signal $S_S$ which propagates through the coupler 68 to the detector 72 for superposition with the reference signal $S_R$ at the detector 72.

The sample housing 84 may be associated with a mechanical component and a positioning arrangement which locates a fluid about the mechanical component. The positioning arrangement may facilitate flow of the fluid about the mechanical component to perform any of various functions including chemical, mechanical, hydromechanical, lubricating and cooling functions. The positioning arrangement may be a positioning system which actively moves fluid about the mechanical component, and may include a fluid circuit. The sample housing may be formed in a monitoring circuit which removes fluid material from the positioning arrangement and returns the fluid after it passes through the housing 84. The monitoring circuit may be an analysis loop in a fluid system which supports the function of the mechanical component.

Figure 3:
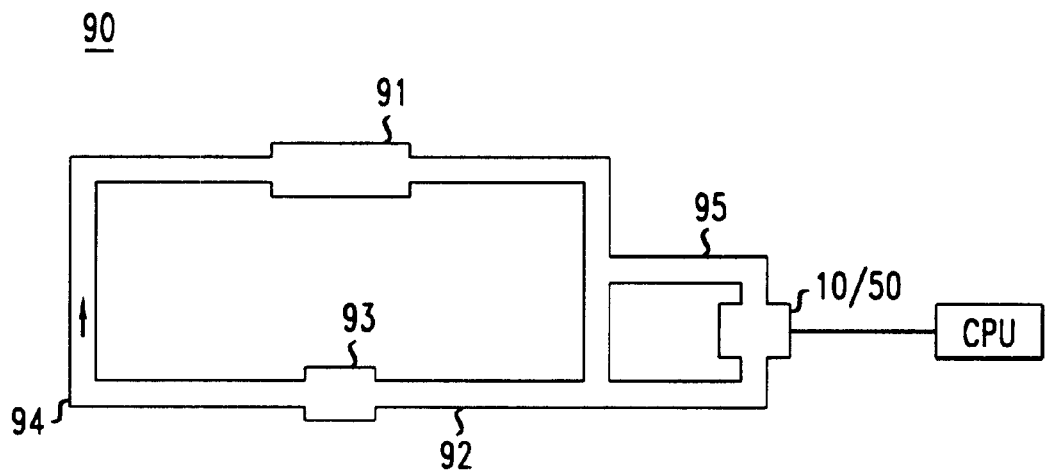
FIG. 3 illustrates a fluid system for in-line monitoring of a characteristic.

This is schematically illustrated in FIG. 3 wherein a system 90 comprises a mechanical component 91 and a fluid positioning system 92, comprising a reservoir 93, a primary flow path 94 and a secondary flow path 89. The reservoir 93 contains the mixture 86. The primary flow path 94 circulates the mixture 86 between the mechanical component 91 and the reservoir 93, and the secondary flow path 95 circulates a portion of the mixture 86 from the primary flow path through the system 10 or the system 50.

Figure 4:
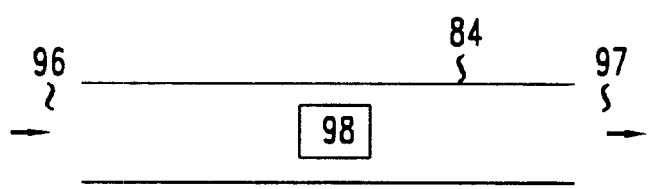
FIG. 4 describes a sample housing suitable for use in the system of FIG. 3.

In the system 90 the sample housing 84 is an open chamber in the sense that portions of the mixture 86 may enter and exit this chamber during analysis. An exemplary sample housing 84 suitable for insertion in the secondary flow path 95 of system 90 is shown in FIG. 4. It includes an inlet 96 for receiving the mixture 86, an outlet 97 for emitting the mixture 86 and an optical flat 98 for transmitting radiation into and out of the housing 84. A processing unit receives intensity information from the detector 30/72 of the interferometric system 10/50 to monitor interference information as a function of time and path length difference between $S_R$ and $S_S$.

By way of example, the system 90 may be a chemical mechanical polishing (CMP) apparatus of the type used to remove material during manufacture of semiconductor products. For a CMP system the mechanical component 91 would correspond to a polishing platen and the mixture 86 would correspond to a slurry which passes along the platen.

More generally, the system 90 may be any mechanical component which operates in association with a fluid. Examples include hydraulic systems, polishing tools, combustion engines and other mechanical assemblies having a liquid medium positioned about a mechanical component.

The following exemplary analysis, applicable to the mixture 86, is based on interference patterns generated with partially coherent light. Generally, the coherence of the light is $$\Gamma(\tau) = \int_0^{+\infty} S(\omega) \cdot e^{-i\omega\tau} d\omega$$

where $\omega$ is $2\pi$ times the frequency; $\tau$ is the time delay between $S_R$ and $S_S$ at the detector; and $S_D$ is the spectral density.

Figure 5:
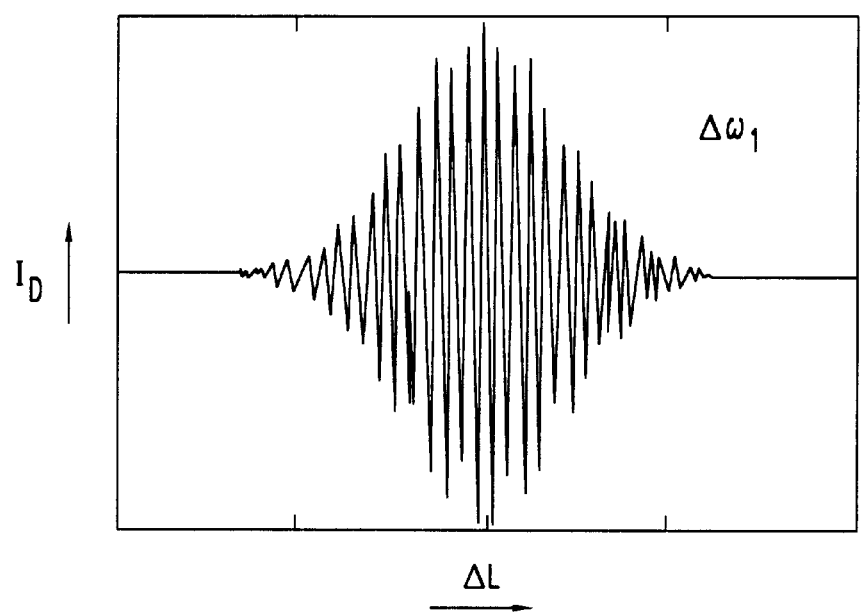
FIG. 5 qualitatively illustrates an interference signal generated by the system of FIG. 1, 2 or 3.

Superposition of the signal at the detector 72 results in intensity at the detector:

$$I_D = I_R + I_S + 2(I_S I_R)^{1/2} \Gamma(k) \cos(k\Delta L)$$

where $k=2\pi f_o$, $\Delta L$ is the difference in path length between the reference path 24a and one path 24b, i.e., between the source 20 and the detector 30. See FIG. 1. In this simplified example, with the source 60 of FIG. 2, an interference packet results as illustrated in FIG. 5. The packet has an approximate length of 30 microns. With the mixture 86 in the sample housing 84 of system 50, multiple paths 24b of light result from diffuse backscattering of light from undissolved particles in the mixture 86. Multiple interference packets result from combination of the reference signal $S_R$ with the multiple paths 24b of light.

Figure 6:
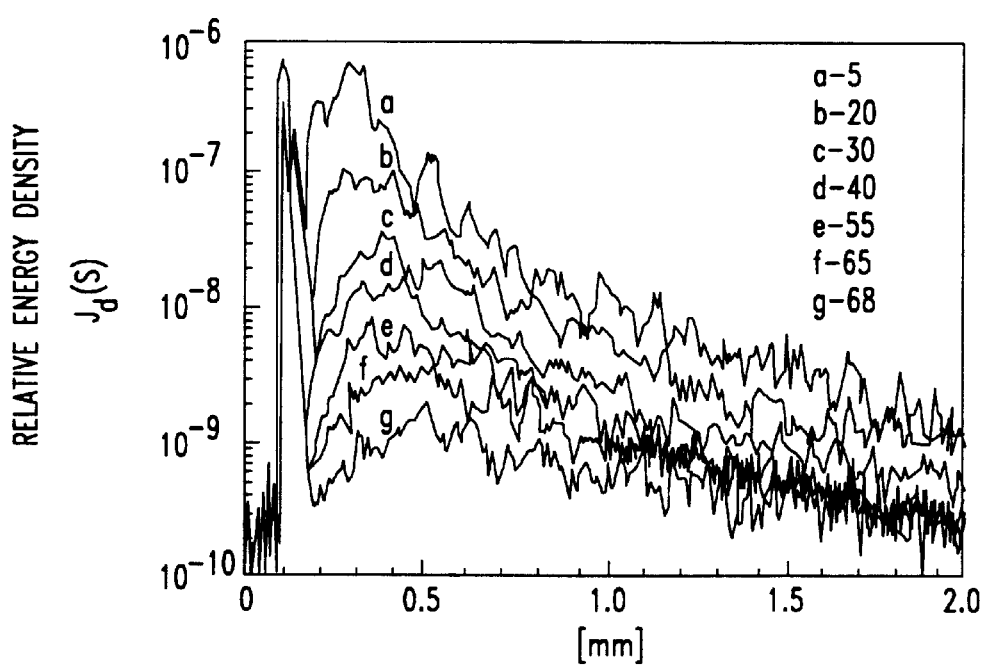
FIG. 6 presents a series of energy density curves obtainable with the system of FIG. 2.

FIG. 6 illustrates a family of energy density curves obtained from analysis of the mixture 86 over a period of sixty-eight minutes. That is, each of the curves a through g illustrates a continuum of interference intensities generated at the detector as the path length $\Delta L$ traversed by the reference signal $S_R$ is modified relative to the each pathlength of backscattered light. In this illustration, displacement of the mirror 78 results in modification of the path length by up to two mm. In the region, at approximately 0.1 mm displacement, each curve has a characteristic peak corresponding to a reflection of the signal from the optical flat. When this peak is subtracted out it can be seen that the series of curves a through g illustrates a general decay in signal value, corresponding to sedimentation of the particles. That is, as particles in the mixture 86 settle, the degree of back scattering diminishes and the intensity of the interference signal associated with back scattered light drops off. The change in energy density over time is proportional to the particle sedimentation rate. Thus, the colloidal stability of the mixture 82 can be assessed over an arbitrary period of time by measuring the signal intensity at the detector 72 for a fixed mirror position, i.e., a nonvarying path length for the reference signal $S_R$.

Figure 7:
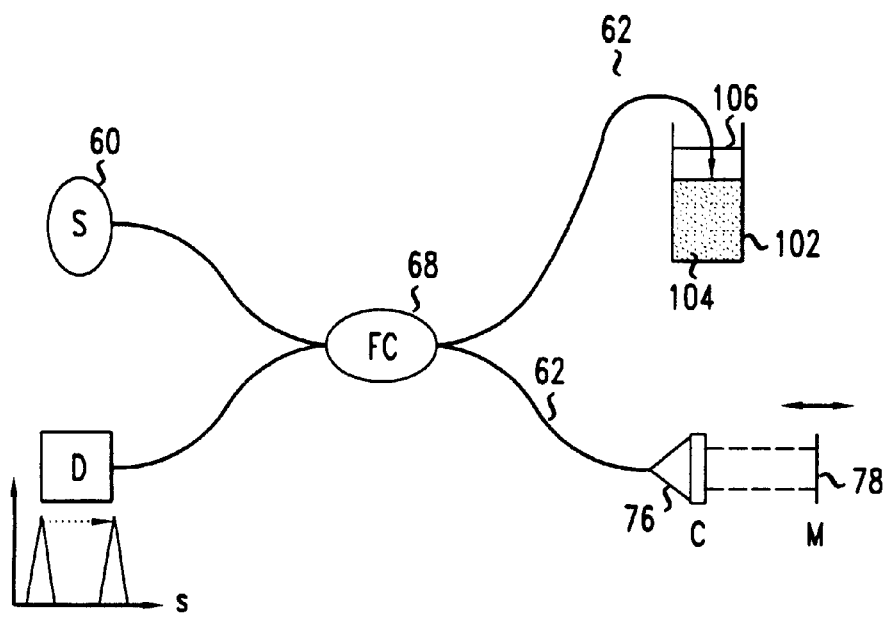
FIG. 7 presents in greater detail another exemplary system for determining a mixture characteristic according to the FIG. 1 illustration.
Figure 7:
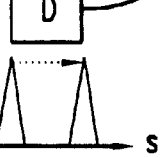

In another arrangement for measurement of colloidal stability, FIG. 7 illustrates a system 100 according to the invention. Like reference numerals in FIGS. 2 and 5 correspond to like components. In lieu of having the fourth segment of fiber 62 extend toward a sample housing, the system 100 differs from the system 50 in that the segment of fiber 62 is positioned to transmit light toward and receive reflected light from a position above a vessel 102 containing a mixture 104. The mixture is illustrated at a point in time when suspended particles have settled an observable distance beneath the open surface 106 of the mixture 104. As sedimentation occurs the optical path length associated with back scattering shifts. This shift, resulting in a fluctuation in the intensity of signal at the detector 72 provides an indication of colloidal system instability. The effect is illustrated in FIG. 8 for a monodispersed mixture of one percent concentration suspended silica particles.

Figure 8:
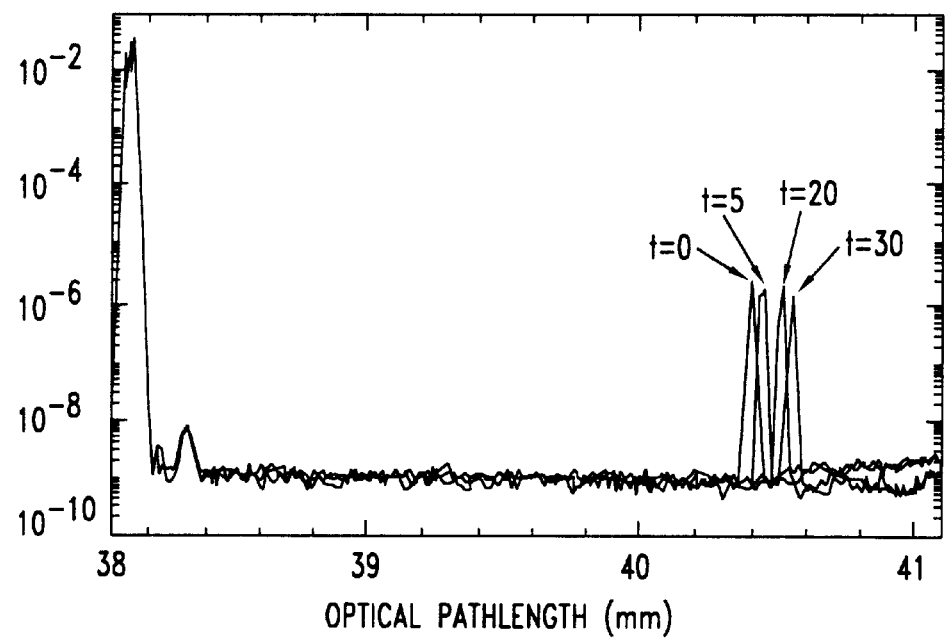
FIG. 8 summarizes data relating sedimentation to changes in optical pathlength.
Figure 9:
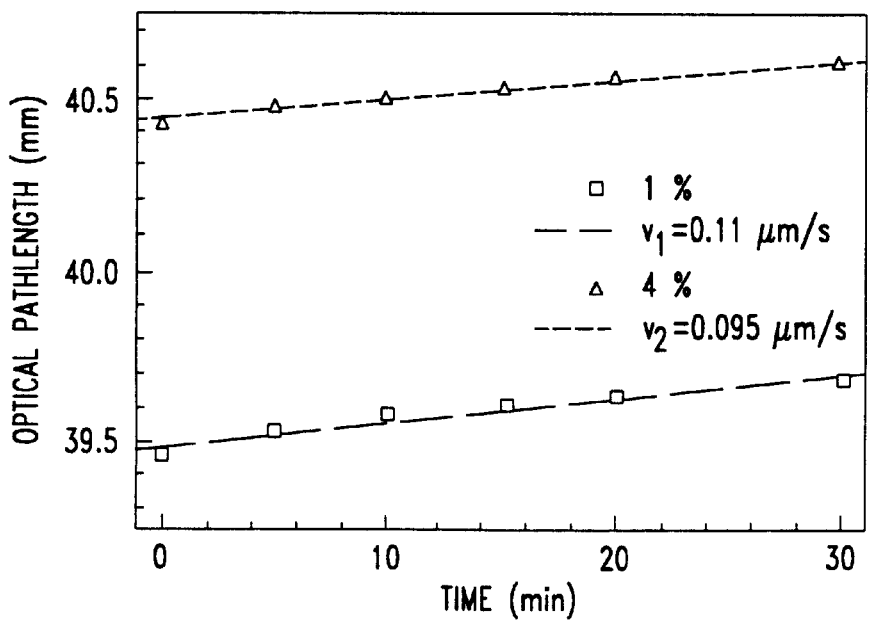
FIG. 9 illustrates a relationship between sedimentation rate and changes in optical pathlength.

The data of FIG. 8 comprises four measurements taken during a 30-minute period. The peak occurring near the 38 nm position corresponds to the Fresnel reflection coming from the open surface of the liquid. This may be used to establish a reference position with respect to which the distance traveled by the sedimenting particles can be evaluated. During each of the four illustrated measurements a somewhat smaller signal peak occurs between 40 and 41 nm. The shift in the position of the peak corresponds to the distance beneath the reflective surface 106 that all of the particles have settled. That is measured movement in the interference pattern corresponds to general increases in the pathlength of back-scattered light during particle sedimentation. This time sequential pattern of intensity peaks as a function of optical pathlength is a reliable indicator of sedimentation rate. See, for example, FIG. 9 which illustrates the change in optical pathlength as a function of time for the suspended silica particles at one percent concentration and four percent concentration. The sedimentation rates ($v_1$ for the one percent concentration and $v_2$ for four percent concentration) are based on the slope of each associated plot.

Application of the system 100 has been illustrated for a simple colloidal system comprising monodispersed particles. That is, because all of the particles have approximately the same size, all of the particles have approximately the same net velocity in the direction of gravitational movement. The same principals apply to a colloidal system comprising a relatively wide distribution of particle sizes. Shifting peaks in the detector signal correspond to reflectors occurring near the trailing edge of the settling particles.

Measurements to characterize sedimentation rates and monitor colloidal stability have been illustrated with systems that measure interference patterns with light signals reflected from a mixture, e.g., by back scattering. Similar measurements may generally be made based on a transmissive optical path through the medium of interest. However, a conventional interferometric system, comprising a partially coherent source, may not provide sufficient dynamic range to determine sedimentation velocity. In the past such transmission-based optical systems have not been suitable for monitoring the stability of dense suspensions having solid components greater than about one percent by volume. According to another aspect of the invention, optical instrumentation can be configured to enable transmissive measurements on particulate suspensions ranging from low concentrations, when ballistic light attenuation is predominant, to high concentrations, when the transmitted light is completely diffused. Such instrumentation incorporates a pair of collimators positioned about a sample chamber to send parallel beams in counter-propagating directions.

Figure 10:
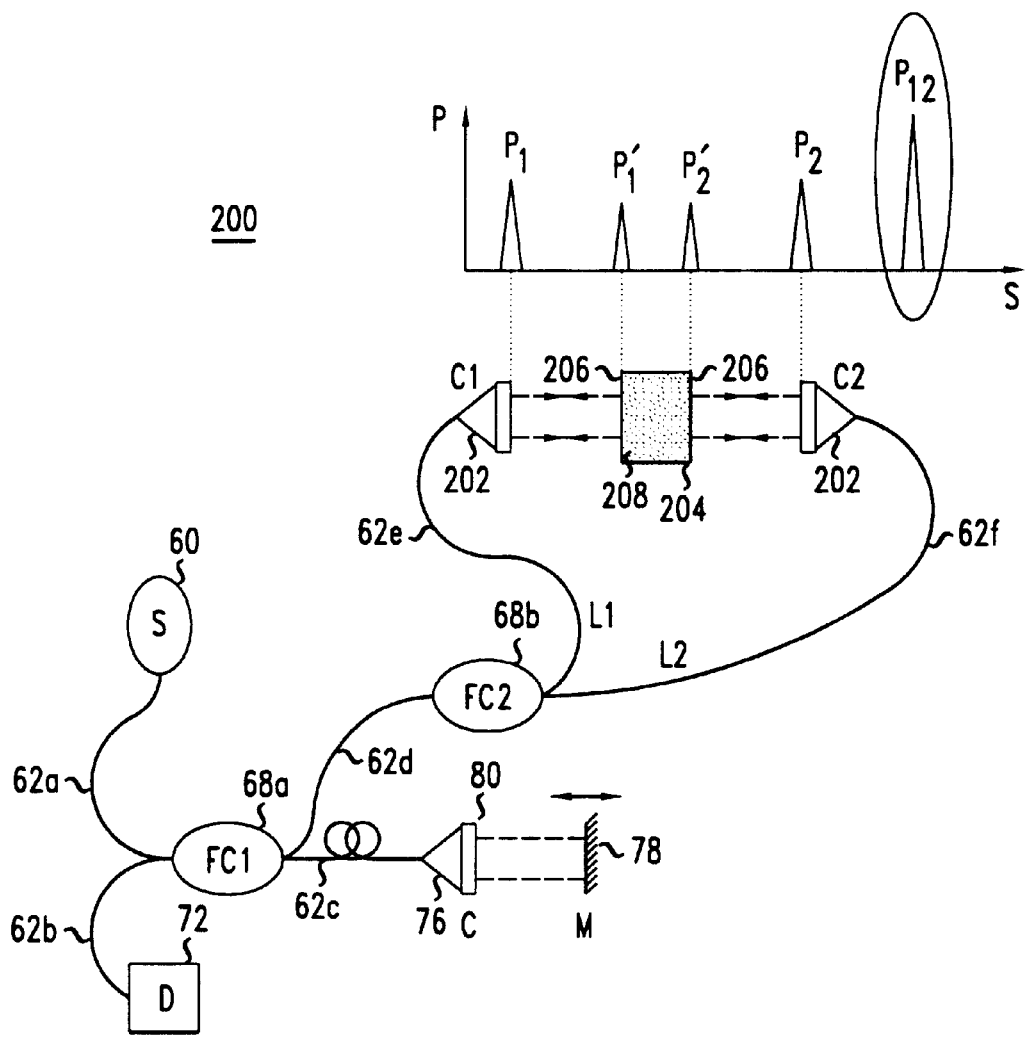
FIG. 10 presents in greater detail still another exemplary system for determining a mixture characteristic according to the FIG. 1 illustration.

The exemplary optical system 200 of FIG. 10 comprises a broadband source 60 such as a superluminescent diode that emits light with a central wavelength of 1.33 micrometers and a FWHM bandwidth of 60 nanometers. Light emitted from the source 60 is coupled directly into one of six single mode optical fibers designated 62a through 62f. The source is connected through the fiber 62a to a first input/output side of a first two-by-two fiber coupler 68a. The light then follows multiple paths along five other segments of fiber. From the same side of the coupler 68a as the source 60 is connected, a second of the fibers 62b is connected to a detector 72.

Third and fourth segments of the fiber are coupled to a second input/output side of the coupler 68a to split the beam of light into two portions each corresponding to a one of the radiation portions 22a and 22b of FIG. 1. One such segment of fiber 62c forms, in conjunction with a collimator 76 and a mirror 78 spaced apart from the collimator 76, a reference arm 80 for providing a reference signal $S_R$. Thus $S_R$ traverses a reference path along three of the fibers 62a, 62b and 62c from the source 60 to the detector 72, corresponding to path 24a of FIG. 1.

The fourth segment of fiber 62d extends to a first input/output side of a second fiber coupler 68b. Fifth and sixth segments of the fiber, each providing substantially the same path length as the other, are coupled to a second input/output side of the coupler 68b. Each such segment of fiber 62e and 62f connects to one of a pair of matched collimators 202 symmetrically positioned about a sample chamber 204 to transmit light to, and receive light from, one another. The collimators 202 are aligned to send parallel beams in counter-propagating directions. The chamber may be open or closed to the atmosphere and is formed with a pair of opposing optical flats 206, each positioned on an opposing side of the chamber 204 to facilitate transmission of light between the collimators 202 and through the chamber 204. A liquid medium 208, comprising a relatively high concentration of suspended particles may be placed in the chamber 204 for analysis.

Thus the source signal Ss traverses a path along four of the fibers 62d, 62e, 62f and 62b and through a medium, e.g., liquid medium 208, to the detector, corresponding to the path 24b of FIG. 1.

The main components of the electric field reaching the detector 72 from the source 60 are $$E_D(t)=E_0(t)\exp(iks)+E_{11}(t)\exp(ikL_{11})+E_{12}(t)\exp(ikL_{12})+E2_1(t)\exp(ikL_{21})+E_{22}(t)\exp(ikL_{22})$$

where $E_{11}$ and $E_{22}$ each correspond to a path that involves reflection on a different one of the collimators 202, while $E_{12}$ represents the field emitted through a first of the collimators 202 and coupled by the second of the collimators 202; and $E_{21}$ is the time-reversed counterpart of $E_{12}$, corresponding to the field emitted through the second of the collimators 202 and coupled by the first of the collimators 202. $L_{i,j}$, i,j=1,2, are the optical pathlengths associated with the fields $E_{ij}$, k is the wave vector, and s is the optical pathlength traveled on the reference arm 80 of FIG. 10.

Based on the above equation for the electric field, the expression for the irradiance at the detector, as a function of the optical pathlength set by the reference mirror 78 of FIG. 10 takes the form $$I_D(s) = I_0 + \sum_{1,j}^{1,2} I_{i,j} g[k(s-L_{ij})]\cos[k(s-L_{ij})]$$

where $I_0$ is a constant term, $I_{i,j}$ is the amplitude of the interference signal given by the summation of the field $E_{i,j}$ with the reference field, and g is the complex degree of coherence associated with the source 60. This irradiance equation gives the position of the interference peaks as the mirror 78 sweeps the reference arm. A qualitative graph of relative intensity of the resulting interference peaks P1, P2 and P12 is shown in FIG. 10 as a function of distance which the mirror 78 alter the path length $S_R$. Interference peaks $P_1$, $P_1'$, $P_2'$ and $P_2$ are each shown in alignment with an associated major reflection. For example, peak $P_1$ is aligned with a reflective surface of one collimator 202 and peak $P_2$ is aligned with a reflective surface of the other collimator 202. With $L_{12}=L_{21}$, the peaks associated with $I_{12}$ and $I_{12}$, are spatially coincident for each identical path of multiple reflection through the medium 208. This is illustrated by the relatively large peak $P_{12}$ of the FIG. 10 graph. As the density of the colloidal suspension, i.e., the medium 208, increases, the width of the peak $P_{12}$ broadens.

Particle size distributions in colloidal suspensions can be determined with an interferometric system such as described for the system 200, incorporating a pair of collimators positioned about a sample chamber to send parallel beams in counter-propagating directions. Sedimentation rate is dependent in part on particle mass and volume. With a suspension of particulates under a controlled gradient, such as a gravitational, magnetic or electric field, measurement of optical transmission through a colloidal dispersion as particles settle provides sufficient information to determine the distribution of size. Generally, when a controlled gradient is added to a colloidal suspension of particulates, it is possible to determine the particle size distribution by following the time dependence of the particle concentration which, in turn, determines the optical transmission through the colloidal dispersion.

Figure 11:
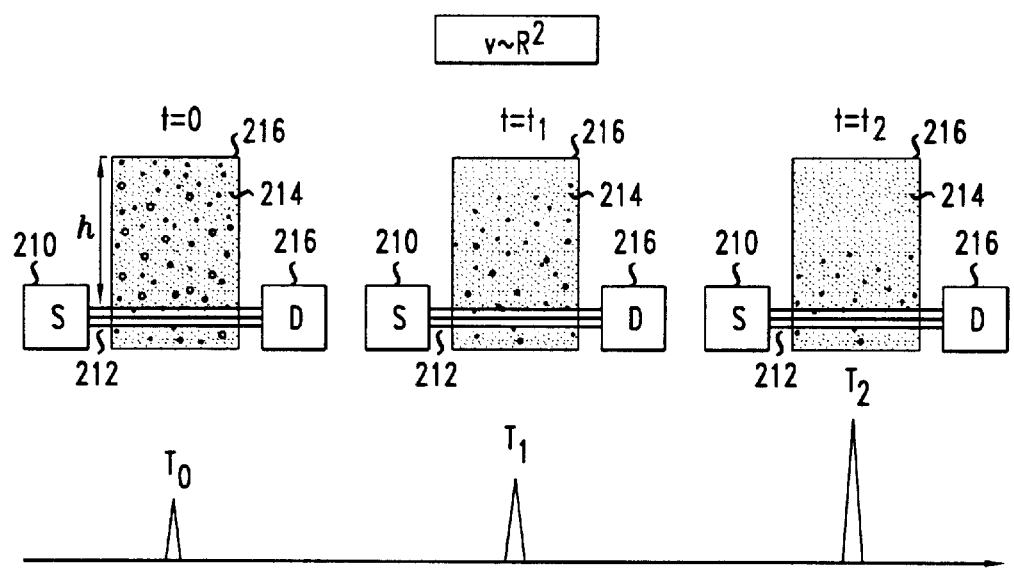
FIG. 11 provides a simple example of sedimentation to illustrate principles according to the invention.

For purposes of providing a simplistic illustration a trimodal suspension is shown to undergo sedimentation in the sequential views of FIG. 11. In each view a source 210 passes a beam 212 through a sample of a colloidal suspension 214 to a detector 216. The suspension has a surface region 218 above the beam which is useful to establish a reference height h relative to the beam. Initially the suspension comprises a homogeneous distribution of small, medium and large particles. Under a normal gravitational field the transmission T is shown to be an increasing function over time, t. The time origin is set at the moment when the homogeneous suspension is place in front of the beam. At time t=0, with large, medium and small particles homogeneously distributed, the detector 216 receives an initial signal $T_0$ from the source 210. For an initial period of time transmission through the sample has a constant value. This period extends for so long as the overall concentration of particles is constant at the depth h below the surface.

The particles gradually sink from the maximum height, h. At $t=t_1$ all of the large particles have settled beneath the beam 212 and the intensity of the detected signal has increased from $T_0$ to $T_1$ since the class of largest particles in no longer present in the region where the light beam is passing through the sample. At time $t=t_2$ all of the medium particles have fallen below the beam 212 and the signal magnitude has increased to $T_2$.

For a heterogeneous distribution of particle sizes, the transmission, T, has the Lambert-Beer form given by:

$$T = \exp\left(-L\sum_i N_i \sigma_i\right)$$

where L is the thickness of the sample, $N_i$ and $\sigma_i$ are the concentration and scattering cross section of the class of particles characterized by the radius $R_i$. The above relationship for transmission holds for systems of non-interacting particles, which is the case whenever the concentration of the suspension is relatively low, i.e., less than ten percent. Since the measurements in a heterogeneous medium are taken at discrete times $t_k$, the transmission at two successive moments in time takes the form $$\ln(T_k) = \ln(T_{k-1}) + LN_k \sigma_k$$

where $T_k$ and $T_{k-1}$ are the transmissions measured at the moments $t_k$ and $t_{k-1}$, respectively, while $N_k$ and $\sigma_k$ characterize the particles that depleted the region of investigation during the period $\Delta t_k = t_k - t_{k-1}$ . . . It follows that the concentration of these particles is $$N_k = \frac{1}{L\sigma_k} \ln\left[\frac{T_k}{T_k - 1}\right]$$

The scattering cross section $\sigma_k$ is derivable from the following form of Stokes law:

$$R_{(k)} = \left[\frac{9\eta h}{2(\rho_s - \rho_l)gt}\right]^{\frac{1}{2}}$$

where $\eta$ is the viscosity coefficient of the suspending liquid, $\rho_s$ and $\rho_l$ are the densities of the particle and suspending liquid, respectively, and g is the gravitational acceleration. Using the refractive index of both the liquid and the suspended particles, the cross section $\sigma_k$ can be calculated from Mie Theory at each moment of time. See, for example, Kokhanovsky, *Optics of Light Scattering Media: Problems and Solutions*, John Wiley & Sons, 1999, at Appendix II which provides solutions for light scattering cross sections as a function of radius for spherical particles. However, numerical computations according to Mie theory are believed to be most suitable for applications disclosed herein.

Based on the foregoing, by monitoring the transmission evolution in time, one can approximate the sizes of the particles present in the mixture and the particle concentration associated with each size. The approximation may be most easily computed with mathematics appropriate for spherical particles. Other, perhaps more complex, approaches may be applied as well. However, for purposes of inferring the relative distribution of particle sizes, or monitoring shifts in this distribution, spherical approximations have been found to render useful results. This is further described with reference to FIGS. 14 and 15 herein.

It should be noted that when the particles are spherical, no approximations are involved in evaluating the associated scattering cross sections. During measurement, each moment in time corresponds to a specific particle size within the system limits of dynamic range. This dimensional information can be evaluated and further used to calculate the corresponding cross section with great precision using a simple computer routine. With this method no information about initial concentration of particles is needed.

A very large dynamic range is available with an interferometric system incorporating a pair of collimators positioned about a sample chamber to send parallel beams in counter-propagating directions, e.g., the system 200 has a dynamic range of approximately 80 dB, and, dynamic ranges as high as 150 dB appear achievable. Due to the large dynamic range of the system detection used, the particle size distribution can be obtained for concentration suspensions.

Figure 12:
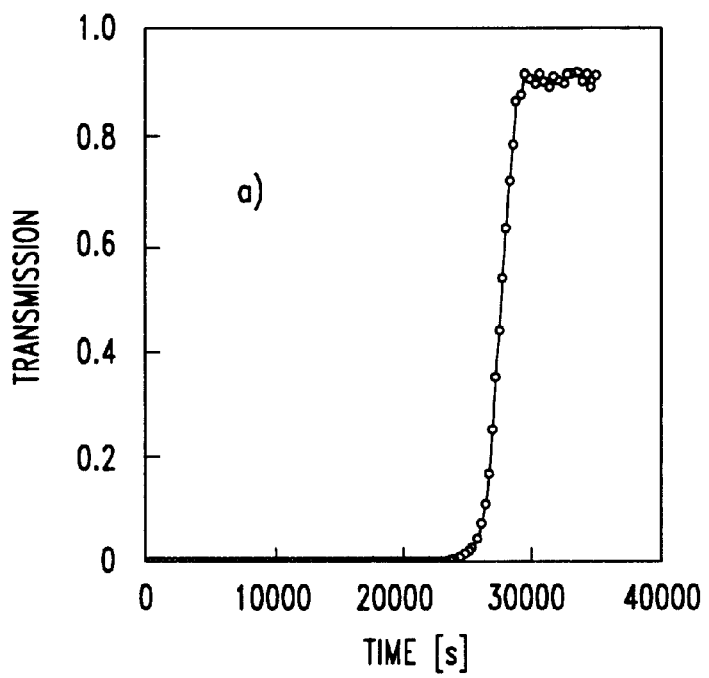
FIG. 12 illustrates changes in transmission through a suspension as measured with the system of FIG. 10.
Figure 13:
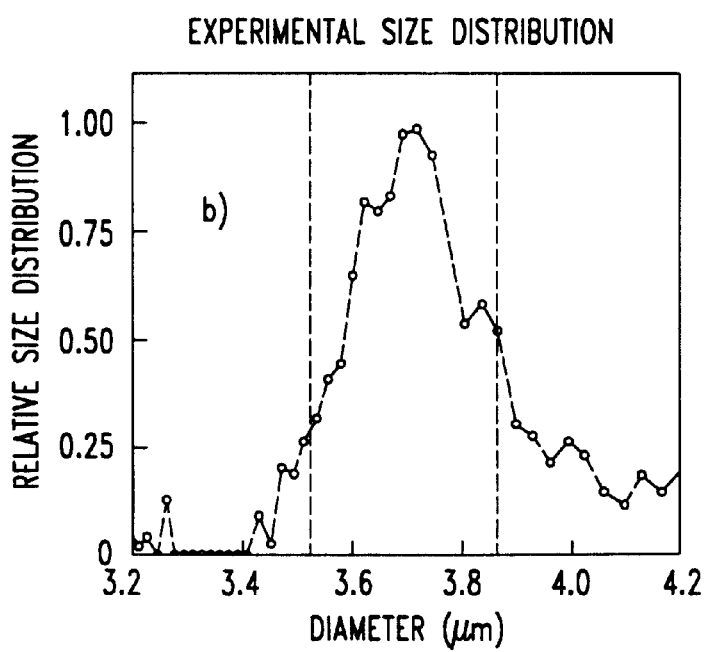
FIG. 13 illustrates an experimentally derived distribution of particle sizes for a suspension.

This methodology was applied to suspensions of standard 3.7 micron polystyrene microspheres. The polystyrene microspheres are characterized by a refractive index of 1.59, and a density of 1.05 relative to water. Water was used as the suspending liquid. FIG. 12 shows the time evolution of the measured transmission over a period of 10 hours. The steep slope of the experimental curve indicates that the polystyrene suspension is highly monodispersed. This is confirmed by the computed particle size distribution, based on $N_k$ acccording to the aforedescribed procedure. FIG. 13 indicates the location of the peak value of $N_k$ as being between 3.6 and 3.8 microns. The experimental evaluation of this suspension is consistent with the above-stated specifications as provided by the manufacturer of the polystyrene microspheres.

Figure 14:
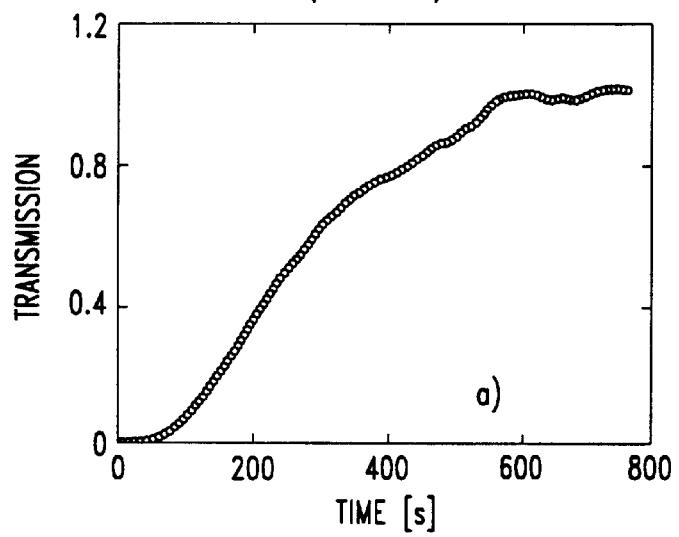
FIG. 14 illustrates changes in transmission through a second suspension as measured with the system of FIG. 10.
Figure 15:
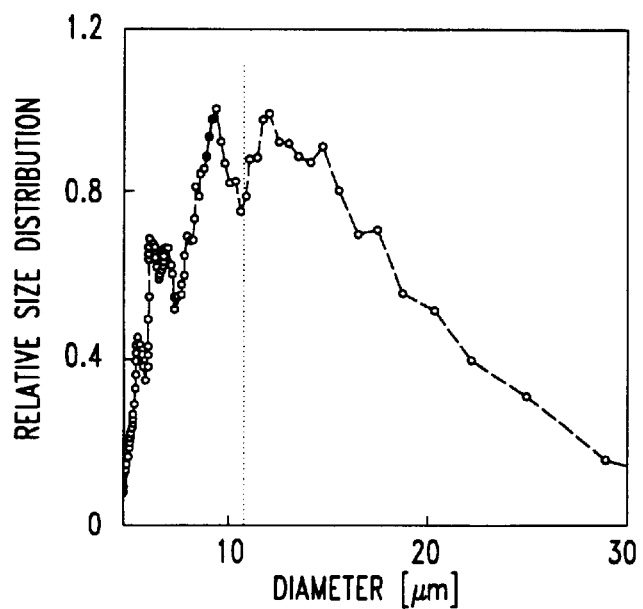
FIG. 15 illustrates an experimentally derived distribution of particle sizes for the second suspension.

The method has been further applied to characterize alumina powder of (10.2+/−0.4) microns. A solution was made by mixing powder with deionized water and the sample was sonicated for several minutes to limit the aggregation process. Experimental results for the time-dependent transmission and particle size distribution are illustrated in FIGS. 14 and 15. Measurements were taken with the system 200. It can be seen that the particle size distribution of FIG. 15 is broad relative to that derived for the polystyrene microspheres (FIG. 13). It can be inferred from this data that particle size was unstable. This conclusion is consistent with agglomeration characteristics of the suspension. It should also be noted that the size distribution of the agglomerated species is based on equivalent spherical particles that would sediment with the same velocity as the real particles. While details relating to actual particle shapes are difficult to determine, information derived from spherical assumptions is sufficient in many applications, particularly when the objective is to monitor general characteristics of mixtures or temporal changes in particle size distribution. In some circumstances the details of particle shape are not critical to accurate determination of particle size distribution.

To reduce the time necessary for measurement of suspensions containing small particles, a centrifugal experimental design can be applied, as is common for many sedimentation investigations. Some of the disclosed embodiments illustrate use of optical couplers and fiber optics. While use of these improves the convenience and efficiency of systems constructed according to the invention, these are not required. Conventional beam splitters and other types of light sources may be used to construct the systems disclosed in the figures.

Numerous example embodiments of invention have been described. It will be apparent to those of skill in the art that other configurations, component substitutions, and alterations may be incorporated without departing from the spirit and scope of the invention, which are only limited by the claims which follow.

What is claimed:

1. A method of characterizing particles in a liquid medium, comprising:

a. introducing the liquid medium into a container, wherein the liquid medium is stationary,
    b. allowing particles in the liquid medium to settle,
    c. exposing the particles in the liquid medium to a sampling beam, the sampling beam being stationary with respect to the container,
    d. measuring, during a period in which the particles undergo sedimentation, changes in the intensity among interference patterns generated by combining first and second partially coherent radiation portions, each generated from the same source, the first portion including a component of the sampling beam after exposure to the particles, the second portion transmitted through a reference path.

2. The method of claim 1 including the steps of:
    determining the difference in path length traversed by the first and second radiation portions before the first and second portions are combined; and
    relating the determined path length difference to the measured intensity.

3. The method of claim 2 including the step of determining sedimentation rate of suspended particles based on changes in intensity among the interference patterns.

4. The method of claim 1 further including:
    determining the concentration of suspended particles based on changes in measured intensity levels among interference patterns as the particles undergo sedimentation.

5. The method of claim 3 wherein the concentration determination includes determination of the scattering cross section of suspended particles based on Mie theory.

6. The method of claim 3 wherein the concentration determination includes determination of the scattering cross section and particle size based on a spherical approximation of particle size and shape.

7. The method of claim 3 including determining the relative distribution of particle size in the suspension based on the combination of:
    concentration of suspended particles derived from said measured intensity levels;
    estimation of particle size; and
    estimation of particle scattering coefficients.

8. The method of claim 3 including determining the relative distribution of particle size in the suspension based on the combination of:
    concentration of suspended particles derived from said measured intensity levels;
    estimation of particle size according to a form of Stokes law; and
    estimation of particle scattering coefficients based on Mie theory.

9. The method of claim 8 wherein the estimations of particle sizes and scattering coefficients are based on spherical approximations of particle shape and size.

* * * * *